United States Patent [19]
Birdsall et al.

[11] Patent Number: 5,977,184
[45] Date of Patent: Nov. 2, 1999

[54] QUERCETIN CHALCONE AND METHODS RELATED THERETO

[75] Inventors: Timothy C Birdsall; Al F Czap, both of Sandpoint, Id.

[73] Assignee: Thorne Research, Inc., Sandpoint, Id.

[21] Appl. No.: 08/528,682

[22] Filed: Sep. 15, 1995

[51] Int. Cl.$^6$ .................................................. A61K 31/12
[52] U.S. Cl. .......................................... 514/685; 568/334
[58] Field of Search .............................. 568/334; 814/685

[56] References Cited

PUBLICATIONS

Kiehlmann, J. Nat Prod. 58 (3), 450–5, Mar. 1995.
Chopin and Chadenson, "Synthesis of alphitonin, mesopin, and 2,4,6–trihydroxy–2–benzyl–3 coumaranone," *Comptes Rendus Hebdomadaires des Seances de l'Academie des Sciences, Serie C 263*(11): 729–731, 1966.(Plus CA Abstract #66:10803).
Aubry and Chopin, "Synthesis of racemeic dimethylpinobanksin, trimethylaromadendrin and tetramethyltaxifolin," *Bulletin de la Societe chimique de France* 12: 4503–4510, 1971. (Plus CA Abstract #76:113021).
Birch et al., "The Structure of Alphitonin," *J Chem. Soc.*, pp. 3593–3599, 1960.
Clark–Lewis and Jemison, "Reinvestigation of the Supposed Enediol Diacetate Derived, from Dihydroquercetin 5,7,3', 4'–Tetramethyl Ether: Novel Ring–Fission of Dihydroquercetin 5, 7, 3', 4'–Tetramethyl Ether to α,2'–Diacetoxy–3,4, 4',6'–Tetramethoxychalcone," *Tetrahedron Letters* 35: 4179–4182, 1966.
Hergert et al., "The Methylation of Dihydroquercetin," *J. Org. Chem. 21*: 304–310, 1956.
Ravanel et al., Uncoupling Activities of Chalcones and Dihydrochalcones on Isolated Mitochondria from Potato Tubers and Mung Bean Hypocotyls, *Phytochemistry 21*(12): 2845–2850, 1982.
Brandt et al., "Metabolites from the Purple Heartwood of Mimosoideae. Part 3. *Acacia crombei* C.T. White: Structure and Partial Synthesis of Crombenin, A Natural Spiropeltogynoid," *Journal o the Chemical Society. Perkin Transactions I*: 1879–1883, 1981.

Agrawal et al., "Synthesis of Proanthocyanidin; A New Leucocyanidin Trimer (4–8, C–O–C)," *Current Science 48*(15): 661–663, 1979.
Ferreira et al., "Parameters regulating the α–and β–Cyclization of Chalcones," *Journal of the Chemical Society. Perkin Transactions I*: 1437–1446, 1975.
Brandt et al., "Structure and Synthesis of Crombenin, a Natural Spirocoumaranone," *Journal of the Chemical Society. Chemical Communication* (7): 392–393, 1972.
Krishnamoorthy and Seshadri, "Preparation of Flavylium Salts from Dihydroflavonols," *Indian Journal of Chemistry 6*(8): 469–470, 1968.
Clark–Lewis and Jemison, "Synthesis of α,2'–Diacetoxy–3, 4,4',6'–Tetramethoxychalcone and 4,6,3',4'–Tetramethoxyisoaurone," *Aust. J. Chem. 21*:815–816, 1968.
Tominaga, T., "Isomerization of Astilbin. I.," *Journal of the Pharmaceutical Society of Japan 80*(9): 1202–1206,1960.
Bhardwaj et al., "Constitution of Dinatin," *Indian J. Chem. 4*: 173–176, 1966.
Chandorkar et al., "Anthoxanthins: Part XII—Synthetic Approaches to 5–Hydroxylated Leucoanthocyanidins," *J. Sci. Industr. Res. 21B*: 24–27, 1962.
Anand et al., "Synthesis of Certain Partial Methyl Ethers of Flavonols: Rhamnetin, 3–O–Methyl Quercetin, 3,3'–O–Dimethyl Quercetin, Ombuin, 3,7–O–Dimethyl Gossypetin & Reso–oxyayanin–A," *J. Sci. Industr. Res. 21B*: 322–329, 1962.

*Primary Examiner*—Robert Gerstl
*Attorney, Agent, or Firm*—Seed and Berry LLP

[57] ABSTRACT

Quercetin chalcone, an effective, soluble and bioavailable bioflavonoid, is disclosed. Also disclosed are compositions containing quercetin chalcone in combination with an acceptable carrier and/or diluent, as well as methods for administration thereof to warm-blooded animals. Such administration is beneficial in generally maintaining good health of the animal and, more specifically, for the treatment of allergies.

7 Claims, No Drawings

QUERCETIN CHALCONE AND METHODS RELATED THERETO

TECHNICAL FIELD

The present invention relates to a quercetin derivative, quercetin chalcone, as well as compositions and methods for preparation and use thereof.

BACKGROUND OF THE INVENTION

Bioflavonoids are a group of naturally occurring compounds and are widely distributed among plants, including most all citrus fruits, rose hips and black currants. Such compounds are generally isolated from the rinds of oranges, tangerines, lemons, limes, kumquats and grapefruits by commercial extraction methods.

Bioflavonoids have been determined to be involved with homeostasis of the walls of small blood vessels. In addition, these compounds have been found to contribute to the maintenance of normal blood vessel conditions by decreasing capillary permeability and fragility. Bioflavonoids have also been found to have activity as a histamine release blocker (treatment of allergies), a xanthine oxidase inhibitor (treatment of gout), an aldose reductase inhibitor (prevention of diabetic complications), a phospholiphase A2 and lipoxygenase inhibitor (anti-inflammatory), an aerobic glycosis inhibitor (an anti-cancer agent), and a tumor necrosis factor potentiator (an antiviral agent.

However, despite their promise for a variety of medicinal applications, the utility of bioflavonoids have been limited by their poor absorption into the bloodstream due, at least in part, to their low solubility under physiological conditions. For example, quercetin (i.e., 3,3',4',5,7-O pentahydroxyflavone), has been the subject of extensive study, and has the following structure

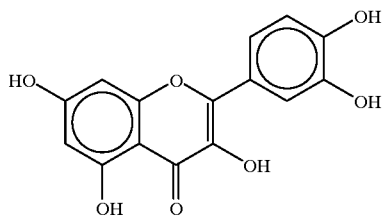

Quercetin is absorbed to the extend of about 1% from an oral dose. Effective cellular uptake of quercetin appears to require the use of water-miscible solvents such as dimethylsulfoxide. Furthermore, while other bioflavonoids have been found to be more soluble than quercetin under physiological conditions, these compounds appear to be less effective than quercetin.

Chalcones, a class of bioflavonoids, have shown promise in overcoming the limitations of other bioflavonoid compounds, and have the following general structure.

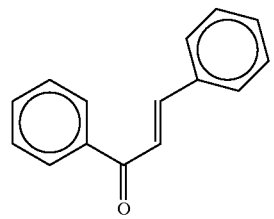

Although chalcones generally have high solubility and absorption under physiological conditions (e.g., hesperidin methyl chalcone, a representative class member, is absorbed to the extend of 60% from an oral dose), their activity is significantly less than that of similar bioflavonoids such as quercetin. This greater solubility and absorption of chalcones may be attributed to their increased solubility through substituents such as sugar moieties present in some chalcones and absent in quercetin. The greater solubility and absorption of chalcones thus appears to be at the expense of biological activity.

Accordingly, there is a need in the art for a soluble, bioavailable bioflavonoid that also possesses high bioactivity. The present invention fulfills these needs and provides further related advantages.

SUMMARY OF THE INVENTION

In brief, the present invention is directed to quercetin chalcone. In one embodiment of this invention, methods for the preparation of quercetin chalcone are disclosed. In another embodiment, compositions including quercetin chalcone and an acceptable carrier and/or diluent are disclosed. In a further embodiment, this invention discloses methods of administering quercetin chalcone to a warm-blooded animal to treat a variety of conditions or illnesses, including allergies.

These and other aspects of this invention will be apparent of a reference to the following detailed description.

DETAILED DESCRIPTION OF THE INVENTION

The present invention is generally directed to an effective, soluble and bioavailable bioflavonoid and, more specifically, to quercetin chalcone, which is an effective, soluble and bioavailable quercetin derivative. Quercetin chalcone is more soluble and provides for greater absorption than quercetin under physiological conditions, and thus provides enhanced bioavailability compared to quercetin. The structure of quercetin chalcone (i.e., 2',3,4,4',6'-pentahydroxychalcone) is presented below.

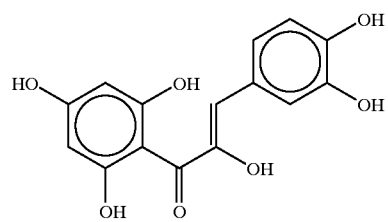

Referring to the above structure, quercetin chalcone has five phenolic hydroxy groups and an enol group (while quercetin has four phenolic hydroxy groups and an enol group). The increased solubility of quercetin chalcone relative to quercetin is due, at least in part, to the additional phenolic hydroxy group. Moreover, unlike other highly soluble chalcone bioflavonoids, the solubility of quercetin chalcone is not accomplished through the presence of other bioactivity-limiting substituents, such as sugar or polysaccharide substituents.

In one aspect of the present invention, a method for preparing quercetin chalcone is disclosed. In this method, quercetin chalcone is prepared from rutin (i.e., quercetin rutinoside) in two steps (1) rutinoside hydrolysis, and (2) chalcone conversion. In one embodiment, the first step is rutinose hydrolysis in which rutin is hydrolized to quercetin. In the second step, quercetin is converted to quercetin chalcone by alkali treatment. Alternatively, in another embodiment, the first step of the method is chalcone conversion, and the second step is rutinose hydrolysis. In a preferred embodiment, rutinose hydrolysis is the first step. In still a further embodiment, quercetin chalcone may be prepared from commercially available quercetin by employing just the chalcone conversion step.

A representative synthesis of quercetin chalcone is described in more detail in Example 1. In one embodiment the synthesis may generally be represented as follows.

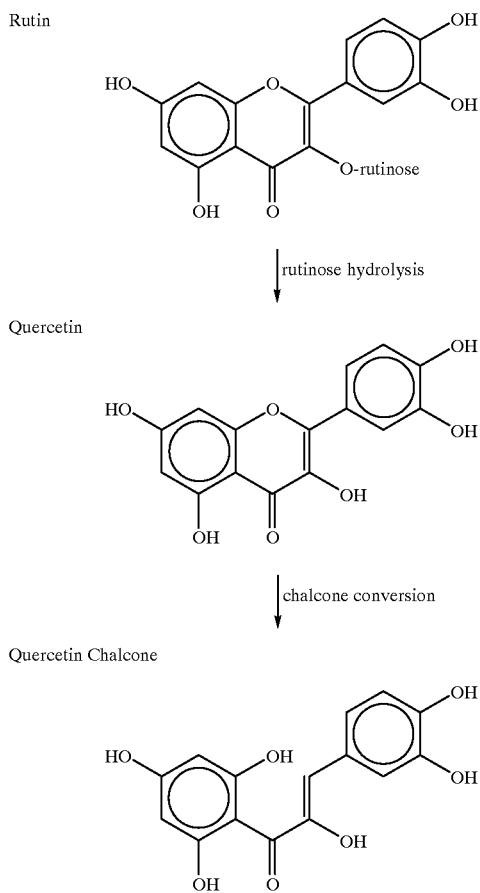

As mentioned above, the rutinose hydrolysis step converts rutin to quercetin by hydrolysis of the glycoside rutinose moiety. The rutinose hydrolysis step may be achieved by either chemical or enzymatic methods. For example, the hydrolysis may be readily accomplished through acidic hydrolysis by treatment of rutin with dilute aqueous acid. Enzymatic rutinose hydrolysis of rutin may be accomplished using the enzyme rhamnodiastase.

In the chalcone conversion step, quercetin is converted to quercetin chalcone by alkali treatment. This may be accomplished by treating quercetin with an aqueous alkali metal salt solution. Suitable alkali metal salts include sodium hydroxide and potassium hydroxide. Upon drying of the alkali reaction mixture, quercetin chalcone is recovered.

In another embodiment of the present invention, compositions containing quercetin chalcone are disclosed. To this end, quercetin chalcone may be formulated for the purposes of administration, as an administratable composition. Such compositions comprise quercetin chalcone and an acceptable carrier and/or diluent, and quercetin chalcone is present in the composition in an effective amount. Preferably, the compositions of this invention include quercetin chalcone for oral or parenteral use in an amount ranging from 1 mg to 5000 mg, more preferably from 10 mg to 2000 mg per dosage, and most preferably from 50 mg to 1000 mg per dosage, and for topical use in an amount ranging from 0.01% to 50%, more preferably from 0.05% to 30%, and most preferably from 0.1% to 20% by weight of the composition. Appropriate concentrations and dosage can be readily determined by one skilled in the art.

Acceptable carriers and diluents are familiar to those skilled in the art. For compositions formulated as liquid solutions, acceptable carriers and diluents include saline and sterile water, and may optionally include antioxidants, buffers, bacteriostats and other common additives. The compositions may be formulated as pills, capsules, granules, or tablets which contain, in addition to quercetin chalcone, diluents, dispersing and surface active agents, binders, and lubricants. One skilled in the art may further formulate quercetin chalcone in an appropriate manner, and in accordance with accepted practices, such as those disclosed in *Remington's Pharmaceutical Sciences,* Gennaro (ed.), Mack Publishing Co., Easton, Pa., 1990 (incorporated herein by reference).

In another embodiment, the present invention provides a method for treating allergies and/or allergic reactins. For example, the compositions may be administered to warm-blooded animals to treat a variety of conditions and illnesses such as hay fever, asthma, allergic rhinitis, sinusitis, allergic conjunctivities and food allergies.

Furthermore, quercetin chalcone plays a role in the homeostasis of small blood vessel walls, and thus may be administered to decrease capillary permeability and fragility. Other pharmacodynamic properties of quercetin chalcone include xanthane oxidase inhibition, and thus has activity as an anti-gout agent, aldose reductase inhibition, and thus has activity in reducing diabetic complications, phospholiphase A2 and lipoxy genase inhibition, and thus has activity as an anti-inflammatory agent, aerobic glycosis inhibition, and thus has activity and an anti-cancer agent, and tumor necross factor potentiation, and thus has activity as an anti-viral agent. In addition, quercetin chalcone prevents lipid peroxidation by decreasing lysosomal enzyme secretion, making it a potent antioxidant suitable for long-term health maintenance.

Methods of the present invention include administering quercetin chalcone to an animal in need thereof in an amount sufficient to treat the condition or illness, or to maintain good health, including systemic administration of quercetin chalcone, preferably in the form of an administratable composition. As used herein, systemic administration includes oral and parenteral methods of administration. For oral administration, suitable administrable compositions of quercetin chalcone include powders, granules, pills, tablets, and capsules as well as liquids, syrups, suspensions, and emulsions. These compositions may also include flavorants, preservatives, suspending, thickening and emulsifying agents, and other acceptable additives. For parenteral administration, quercetin chalcone compositions can be prepared in aqueous injection solutions which may contain, in addition to quercetin chalcone, buffers, antioxidants, bacteriostats, and other additives commonly employed in such solutions.

For topical application, the compositions of this invention may be formulated as solutions, creams, gels and ointments. The compositions may also be formulated for administration to skin or mucosal tissue by, for example, nasal sprays, bronchial inhalers (liquid or powder), and vaginal or rectal suppositories. In the case of allergy treatment, administration may be accomplished by use of an inhaler or atomizer using known techniques. Similarly, compositions suitable for administration to the eye or ear (such as ophthalmic or optic drops) may be formulated using known techniques.

The following examples are provided for purposes of illustration, not limitation.

EXAMPLES

Example 1

Quercetin Chalcone Preparation

In this example, a representative procedure is disclosed for the preparation of quercetin chalcone.

One hundred (100) grams of rutin was dissolved in one (1) liter of 1N hydrochloric acid at a temperature of 80–90° C., and allowed to react at that temperature for a total of 3 hours, forming a yellowish-brown precipitate. The resultant mixture was allowed to cool to room temperature and the precipitate removed by filtration, with continual washing with distilled water, until a pH of 6.0–6.5 was obtained. The precipitate was dried and redissolved in 90% ethyl alcohol, and filtered to remove impurities, with the alcohol subsequently distilled off. The remaining precipitate was then suspended in 200 ml of distilled water. Gradually, a solution of 1N sodium hydroxide was added, until a clear, golden-brown solution without a precipitate was obtained. This solution was oven dried at a temperature of 70–80° C., yielding a brown powder of quercetin chalcone. The quercetin chalcone produced by this method was soluble in distilled water, a concentration of 20% quercetin chalcone in water was readily produced. Quercetin, on the other hand, was almost totally insoluble in water.

Example 2

Quercetin Chalcone Compositions

In this example, formulations of various representative quercetin chalcone compositions are described.

---
Formula #1
---

Two-piece gelatin capsules were prepared containing

| | |
|---|---|
| Quercetin chalcone | 400 mg |
| Silicon dioxide | 4 mg |

Formula #2

An aqueous nasal spray solution was prepared containing

| | |
|---|---|
| Sterile water | 98.95% |
| Quercetin chalcone | 0.2% |
| Sodium chloride | 0.85% |

Formula #3

A buffered saline ophthalmic solution was prepared containing

| | |
|---|---|
| Sterile water | 98.365% |
| Quercetin chalcone | 0.2% |
| Sodium chloride | 0.42% |

-continued

| | |
|---|---|
| Boric acid | 0.6% |
| Sodium borate | 0.29% |
| Sorbic acid | 0.1% |
| EDTA | 0.025% |

Example 3

Methods of Administration of Quercetin Chalcone Compositions

In this example, representative methods of administering the quercetin chalcone compositions of Example 2 to warm-blooded animals are described.

The encapsulated composition of Formula #1 was administered to a 38-year-old female with long-standing environmental sensitivities and dust and mildew allergies. One capsule was administered four times daily. The patient reported a noticeable relief of symptoms following the second dose, and all symptoms were controlled with 4 capsules (containing a total of 1600 mg of quercetin chalcone) daily.

The nasal spray composition of Formula #2 was administered to a 34-year-old female with chronic allergic sinusitis of over three year's duration. The patient was instructed to use the spray three times daily in each nostril. Within 4 weeks, her symptoms had resolved significantly.

The ophthalmic solution composition of Formula #3 was administered to a 41-year-old female with recurrent allergic conjuctivitis. Two drops were placed in each eye four times per day. After 24 hours, all redness and itching of the eyes had disappeared.

It will be appreciated that, although specific embodiments of the invention have been described herein for the purposes of illustration, various modifications may be made without departing from the spirit and scope of the invention. Accordingly, the invention is not limited except by the appended claims.

We claim:

1. A composition comprising a quercetin chalcone and an acceptable carrier or diluent, the quercetin chalcone having the structure

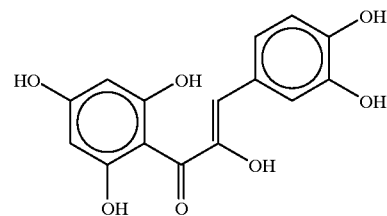

2. The composition of claim 1 wherein the quercetin chalcone is present in the composition in an amount ranging from 1 to 5000 mg.

3. The composition of claim 1 wherein the quercetin chalcone is present in the composition in an amount ranging from 0.01% to 50% by weight.

4. The composition of claim 1 formulated for systemic administration.

5. The composition of claim 1 formulated for oral administration.

6. The composition of claim 1 formulated for parenteral administration.

7. The composition of claim 1 formulated for topical administration to skin or mucosal tissue.

* * * * *